United States Patent
Matsumura et al.

(10) Patent No.: US 9,181,561 B2
(45) Date of Patent: Nov. 10, 2015

(54) ADIPONECTIN-CONTAINING EATING BEHAVIOR CONTROL AGENT FOR ORAL ADMINISTRATION

(75) Inventors: Takeshi Matsumura, Sapporo (JP); Rie Yasuno, Toyohira-ku (JP); Chihiro Sugimoto, Sapporo (JP); Noriko Tabayashi, Kitahiroshima (JP); Uiko Kagaya, Kitahiroshima (JP); Hiroko Miyashiro, Kitahiroshima (JP)

(73) Assignees: Hokusan Co., Ltd., Hokkaido (JP); National Institute of Advanced Industrial Science and Technology, Tokyo (JP); National University Corporation Hokkaido University, Hokkaido (JP)

(*) Notice: Subject to any disclaimer, the term of this patent is extended or adjusted under 35 U.S.C. 154(b) by 757 days.

(21) Appl. No.: 13/146,575

(22) PCT Filed: Jan. 18, 2010

(86) PCT No.: PCT/JP2010/050507
§ 371 (c)(1),
(2), (4) Date: Oct. 31, 2011

(87) PCT Pub. No.: WO2010/087243
PCT Pub. Date: Aug. 5, 2010

(65) Prior Publication Data
US 2012/0115776 A1 May 10, 2012

(30) Foreign Application Priority Data
Jan. 29, 2009 (JP) ................. 2009-018455

(51) Int. Cl.
| C12N 15/16 | (2006.01) |
| A23L 1/305 | (2006.01) |
| A61K 38/22 | (2006.01) |
| A01H 5/08 | (2006.01) |
| C07K 14/475 | (2006.01) |
| C12N 15/82 | (2006.01) |
| C07K 14/575 | (2006.01) |

(52) U.S. Cl.
CPC ............ *C12N 15/8257* (2013.01); *A23L 1/305* (2013.01); *A23L 1/3053* (2013.01); *A61K 38/22* (2013.01); *C07K 14/5759* (2013.01)

(58) Field of Classification Search
None
See application file for complete search history.

(56) References Cited

U.S. PATENT DOCUMENTS

| 7,419,955 B2 | 9/2008 | Kadowaki et al. | |
| 2002/0132773 A1* | 9/2002 | Kincade et al. | 514/12 |
| 2003/0176328 A1* | 9/2003 | Rasmussen et al. | 514/8 |
| 2007/0282002 A1 | 12/2007 | Maezono et al. | |
| 2008/0003243 A1* | 1/2008 | Ito et al. | 424/269.1 |
| 2010/0021444 A1 | 1/2010 | Kawakami et al. | |

FOREIGN PATENT DOCUMENTS

| JP | 3018186 B1 | 3/2000 |
| JP | 2004-345968 A | 12/2004 |
| JP | 2007-31302 A | 2/2007 |
| JP | 2008-24647 A | 2/2008 |
| JP | 2008-63289 A | 3/2008 |
| JP | 2008-63293 A | 3/2008 |
| JP | 2008-105945 A | 5/2008 |
| JP | 4147220 B2 | 6/2008 |
| WO | WO 2007/087468 A2 | 8/2007 |

OTHER PUBLICATIONS

Maeda et al (Biochem. Biophys. Res. Commun. 221, pp. 286-289, 1996).*
Berberich et al (Journal of Plant Physiology, 162(10), pp. 1169-1176, 2005).*
Kubota et al (Cell Metabolism, 6(1), pp. 55-68, 2007); cited on IDS.*
Aoki et al., Biotechnology Symposium Abstracts. 2008;26:32-35.
Aoki et al., Biotechnology Symposium Abstracts. 2008;26:81-82.
Arita et al., Adipocyte-derived plasma protein adiponectin acts as a platelet-derived growth factor-BB-binding protein and regulates growth factor-induced common postreceptor signal in vascular smooth muscle cell. Circulation. Jun. 18, 2002;105(24):2893-8. Epub May 20, 2002.
Berg et al., The adipocyte-secreted protein Acrp30 enhances hepatic insulin action. Nat Med. Aug. 2001;7(8):947-53.
Inaba et al., Effects of platelet-derived growth factor on the synthesis of lipoprotein lipase in human monocyte-derived macrophages. Arterioscler Thromb Vasc Biol. Apr. 1995;15(4):522-8.
Ishigami et al., High-density lipoproteins from probucol-treated patients have increased capacity to promote cholesterol efflux from mouse peritoneal macrophages loaded with acetylated low-density lipoproteins. Eur J Clin Invest. Apr. 1997;27(4):285-92.
Kubota et al., Adiponectin stimulates AMP-activated protein kinase in the hypothalamus and increases food intake. Cell Metab. Jul. 2007;6(1):55-68.
Martin et al., Adiponectin is present in human milk and is associated with maternal factors. Am J Clin Nutr. May 2006;83(5):1106-11.
Mitsuhara et al., Efficient promoter cassettes for enhanced expression of foreign genes in dicotyledonous and monocotyledonous plants. Plant Cell Physiol. Jan. 1996;37(1):49-59.
Morena-Manzano et al., Enhancement of TNF-alpha-induced apoptosis by immobilized arginine-glycine-aspartate: involvement of a tyrosine kinase-dependent, MAP kinase-independent mechanism. Biochem Biophys Res Commun. Oct. 22, 2000;277(2):293-8.

(Continued)

*Primary Examiner* — David T Fox
*Assistant Examiner* — Stephen Uyeno
(74) *Attorney, Agent, or Firm* — Wolf, Greenfield & Sacks, P.C.

(57) ABSTRACT

Disclosed is a technique that facilitates the oral ingestion of adiponectin in a large quantity and enables the expansion of the range of use applications of adiponectin. Specifically disclosed is an appetite control agent for oral administration, which comprises adiponectin as an active ingredient. Particularly, the appetite control agent comprises a transformant capable of expressing adiponectin. Also specifically disclosed is a food composition for controlling appetite, which comprises the appetite control agent.

4 Claims, 10 Drawing Sheets

(56) References Cited

OTHER PUBLICATIONS

Nakata et al., CD36, a novel receptor for oxidized low-density lipoproteins, is highly expressed on lipid-laden macrophages in human atherosclerotic aorta. Arterioscler Thromb Vasc Biol. May 1999;19(5):1333-9.

Okamoto et al., An adipocyte-derived plasma protein, adiponectin, adheres to injured vascular walls. Horm Metab Res. Feb. 2000;32(2):47-50.

Ouchi et al., Novel modulator for endothelial adhesion molecules: adipocyte-derived plasma protein adiponectin. Circulation. Dec. 21-28, 1999;100(25):2473-6.

Steinberg et al., Adiponectin: starving for attention. Cell Metab. Jul. 2007;6(1):3-4.

Ueno et al., Adiposcience 2007;4(3):231-238.

Yamauchi et al., Adiponectin stimulates glucose utilization and fatty-acid oxidation by activating AMP-activated protein kinase. Nat Med. Nov. 2002;8(11):1288-95. Epub Oct. 7, 2002.

Yasuno et al., Production and analysis of transgenic plant expressing human adiponectin. BMB 2007 Joint Conference of $30^{th}$ Annual Conference of The Molecular Biology Society of Japan and $80^{th}$ Conference of Japanese Biochemical Society. Nov. 25, 2007. Abstracts. p. 350.

Yasuno et al., Production and analysis of transgenic plant expressing human adiponectin. BMB 2007 Joint Conference of 30th Annual Conference of The Molecular Biology Society of Japan and 80th Conference of Japanese Biochemical Society. Nov. 25, 2007. Abstracts. p. 350.

\* cited by examiner

ADIPONECTIN-CONTAINING EATING BEHAVIOR CONTROL AGENT FOR ORAL ADMINISTRATION

RELATED APPLICATION

This application is a national stage filing under 35 U.S.C. §371 of international application PCT/JP2010/050507, filed Jan. 18, 2010, the disclosure of which is incorporated by reference herein in its entirety.

TECHNICAL FIELD

The present invention relates to an adiponectin-containing appetite control agent.

BACKGROUND ART

Adiponectin is a kind of adipocytokines excreted from adipocytes, and is indicated to be closely related to metabolic syndrome. To date, in order to improve metabolic syndrome, various substances, including lactic acid (Patent literature 1), yeasts (Patent literature 2), hydrothermal extracts of plant worm (Patent literature 3), triglyceride (Patent literature 4), acylamide compounds (Patent literature 5) and others, have been investigated with the aim of facilitating adiponectin production. Meanwhile, there have been attempts by administering adiponectin or fragments thereof into the body to treat or prevent cancers (Patent literature 6), inflammatory diseases (Patent literature 7), arterial sclerosis (Patent literature 8) and others. Furthermore, adiponectin has been reported to activate AMP kinase in the hypothalamus and to increase food intake (Non-patent literature 1), and an appetite control model by adiponectin has been proposed (Non-patent literature 2).

The inventors of the present invention have already searched for the possibility of oral administration of adiponectin, and investigated the biological activity of adiponectin upon its oral administration (Non-patent literature 3); the contents of this study required further investigation and verification.

CITATION LIST

Patent Literature

Patent literature 1: JP A 2008-63289
Patent literature 2: JP A 2008-63293
Patent literature 3: JP A 2007-31302
Patent literature 4: JP A 2008-24647
Patent literature 5: JP A 2008-105945
Patent literature 6: JP A 2004-345968
Patent literature 7: JP B 3018186
Patent literature 8: JP B 4147220

Non-Patent Literature

Non-patent literature 1: N. Kubota et al. (2007) "Adiponectin stimulates AMP-activated protein kinase in the hypothalamus and increases food intake" Cell Metabolism Vol. 6, P55-68. Non-patent literature 2: G. R. Steinberg and B. E. Kemp (2007) "Adiponectin: Starving for Attention" Cell Metabolism Vol. 6, P 3-4.
Non-patent literature 3: Yasuno et al. (2007) "Production and analysis of transgenic plant expressing human adiponectin," BMB 2007 (Joint Conference of 30th Annual Conference of The Molecular Biology Society of Japan and 80th Conference of Japanese Biochemical Society) Abstracts, 350 pages, published on Nov. 25, 2007.

DISCLOSURE OF THE INVENTION

Problems to be Solved by the Invention

A problem to be solved by the invention is to provide a technique for facilitating large-quantity oral intake of adiponectin and for expanding its application range.

Means of Solving the Problem

During research to solve the above problem, the present inventors have attempted to produce transgenic strawberry that produces human adiponectin and to confirm the action of adiponectin upon oral administration of the produced fruit to mice, and the inventors have found an action completely different from that had already been known, i.e., an action to control appetite through its ingestion; after further research, the inventors have achieved the present invention.

Namely, the present invention relates to an appetite control agent for oral administration comprising adiponectin as an active ingredient.

Furthermore, the present invention relates to said appetite control agent for oral administration, comprising a transformant that expresses adiponectin.

In addition, the present invention relates to said appetite control agent for oral administration, wherein the transformant that expresses adiponectin is a transformant in which a gene consisting of
(a) a DNA consisting of the base sequence set forth in SEQ ID NO 1, or
(b) a DNA that hybridizes to a DNA consisting of a complementary base sequence to the DNA consisting of the base sequence of (a) under stringent conditions, and that encodes a polypeptide having an adiponectin activity, is introduced.

Furthermore, the present invention relates to said appetite control agent for oral administration, wherein the transformant that expresses adiponectin is a transformant in which a gene encoding
(a) a polypeptide consisting of the amino acid sequence set forth in SEQ ID NO 2, or
(b) a polypeptide that consists of an amino acid sequence in which one or several amino acids are deleted from, replaced in or added to the amino acid sequence set forth in SEQ ID NO 2, and that has an adiponectin activity, is introduced.

In addition, the present invention relates to said appetite control agent for oral administration, comprising an edible tissue of the transformant that expresses adiponectin.

Furthermore, the present invention relates to said appetite control agent for oral administration, wherein the edible tissue can be eaten raw.

In addition, the present invention relates to said appetite control agent for oral administration, wherein the transformant is a transformed plant.

Furthermore, the present invention relates to said appetite control agent for oral administration, wherein adiponectin is expressed in a transformed plant.

In addition, the present invention relates to said appetite control agent for oral administration, which does not comprise animal-derived ingredients other than the adiponectin expressed in the transformed plant.

Furthermore, the present invention relates to said appetite control agent for oral administration, wherein the ingredients are plant-derived, except the adiponectin expressed in the transformed plant.

In addition, the present invention relates to appetite control agent for oral administration, wherein the plant is strawberry, and the edible tissue is a strawberry fruit.

Furthermore, the present invention relates to a food composition for controlling appetite, comprising said appetite control agent for oral administration.

Effects of the Invention

According to the present invention, an adiponectin-containing appetite control agent for oral administration can be provided, enabling the control of appetite such as increasing food intake, by means of taking such an appetite control agent for oral administration.

In addition, the present invention enables oral intake of adiponectin through the use of an appetite control agent for oral administration. For example, different from direct administration into blood, the inventive agent does not rapidly change blood adiponectin concentrations, resulting in almost no burden to the body. Namely, an adiponectin-containing food composition that has excellent safety and stability can be provided.

EMBODIMENTS FOR CARRYING OUT THE INVENTION

The appetite control agent for oral administration containing adiponectin as an active ingredient according to the present invention acts to enhance or inhibit food intake by being ingested, enabling the control of appetite. As such adiponectin, any animal-derived adiponectin may be used; from the viewpoint of oral intake, those derived from mammals such as human, cow, and pig are preferred.

In the present invention, "appetite control agent for oral administration" may be, for example, those which are prepared by a routine method for formulations in accordance with methods described in "Japanese Pharmacopoeia 15$^{th}$ edition, General Rules for Preparations," and which are suitable for oral intake. Its dosage form includes capsule, granule, pill, powder, tablet, etc.; in addition, the appetite control agents for oral administration may also mix, depending on its dosage form, various additives such as excipient, binding agent, disintegrating agent and coating agent. Furthermore, the appetite control agent for oral administration is not limited to artificially-mixed compositions; it also includes not only various compositions used for foods, but also food materials such as vegetables including leaf, root and fruit, as well as fruits, and final products (food products) processed into drinks and foods, thus encompassing any matters subjected to be eaten.

The appetite control agent for oral administration according to the present invention may comprise a transformant that expresses adiponectin. Said transformant is not particularly limited so long as it does not cause a problem when being ingested, and it does express adiponectin due to transformation. For example, it may be transformed microorganisms such as those conventionally used in food products, including Bacillus natto, lactic acid bacteria, acetic acid bacteria, yeasts, and Basidiomycetes, or transformed animals that highly express adiponectin; it is preferably transformed plants such as rice, wheat, barley, corn, strawberry, tomato, potato, lettuce, soybean, and azuki, considering that they are orally taken and they can avoid the risk of contamination with pathogens (viruses, fungi, bacteria, and parasites) infectious to animals.

In addition, said transformant preferably has an edible tissue. Examples of such edible tissue include a fruiting body of Basidiomycetes (mushroom), fruits of plants (e.g., strawberry fruit, tomato), roots (Japanese radish, potato), leaves (cabbage, lettuce), and seeds (grains suchas rice, barley, wheat, corn, and beans such as soybean, azuki). In particular, edible tissues that can be eaten raw are preferred, because adiponectin does not degenerate due to cooking such as heating, and because of easiness of eating.

Methods for producing transformants are not particularly limited, and generally well-known methods may be used. Examples include transformation methods suitable for various subjects, such as a method of making competent cells by means of calcium method (mainly bacteria), a method using vectors such as phage and plasmid (mainly bacteria), protoplast-PEG method (mainly filamentous fungi), lithium method (mainly yeasts), electroporation method, a method using a particle gun, agrobacterium method (plants), etc.

The transformant expressing adiponectin of the present invention is, in one embodiment, the one in which a gene consisting of (a) a DNA consisting of the base sequence set forth in SEQ ID NO 1, or (b) a DNA that hybridizes to a DNA consisting of a complementary base sequence to the DNA consisting of the base sequence of (a) under stringent conditions, and that encodes a polypeptide having an adiponectin activity, is introduced.

The base sequence set forth in SEQ ID NO 1 represents the translated region and stop codon (85-819) of the human adiponectin gene (NCBI Accession No. NM_004797).

"Stringent condition" herein refers to a condition wherein specific hybrids are formed but non-specific hybrids are not formed. Such a condition is the one which is understood by those skilled in the art, and includes a condition under which nucleic acids having a homology of 99.5% or more can hybridize, but DNAs having lower homologies do not hybridize each other.

The transformant expressing adiponectin of the present invention is, in one embodiment, the one in which a gene encoding (a) a polypeptide consisting of the amino acid sequence set forth in SEQ ID NO 2, or (b) a polypeptide that consists of an amino acid sequence in which one or several amino acids are deleted from, replaced in or added to the amino acid sequence set forth in SEQ ID NO 2, and that has an adiponectin activity, is introduced.

Here, the meaning of "one or several" may vary depending on the site of an amino acid residue in the stereostructure of said polypeptide at which amino acids are deleted from, replaced in or added to, as well as the kind of the amino acid residue; however, "one or several" generally refers to 2-20, preferably around 2-15.

In addition, "having adiponectin activity" means that it has at least one activity possessed by adiponectin; preferably, it has an activity similar to that of the polypeptide consisting of the amino acid sequence set forth in SEQ ID NO 2.

Examples of such adiponectin activities include, for example, activities well known as action by adiponectin, as described in the above-mentioned Patent literature 6 (JP A No. 2004-345968):
(1) in C2C12 cells, AMPK activating action and ACC inhibitory action, glucose-intake promoting activity, fatty-acid oxidization promoting activity (Nat. Med. 8:1288-1295, 2002);
(2) in primary cultured hepatic cells, AMPK activating action (Nat. Med. 8:1288-1295, 2002), and glucose-release inhibitory action (Nat. Med. 7:947-953, 2001);
(3) VCAM-1, ICAM-1, E-selectin in vascular endothelial cells (Circulation 100:2473-2476, 1999);
(4) in macrophages, a decrease in the amount of cholesterol ester (Eur. J. Clin. Invest. 27:285, 1997), a decrease in accumulation of lipid droplets (Arterioscler. Thromb. Vasc. Biol. 19:1333, 1999), scavenger receptor (Biochem. Biophys. Res. Commun. 22:277, 2000), or inhibitory action of lipoprotein lipase (LPL) expression (Arterioscler. Thromb. Vasc. Biol. 15:522, 1995), or inhibitory action of TNF-α production;
(5) inhibitory action of growth and migration of vascular smooth muscle cells (Circulation 105:2893, 2002);
(6) collagen I, III, V binding activity (Horm. Metab. Res. 32:47-50, 2000), etc.

Adiponectin activities can also be easily confirmed by an evaluation system of adiponectin using phosphoenolpyruvate carboxykinase (PEPCK) promoter and luciferase, constructed by the present inventors (refer to Example 3 below "3. Adiponectin evaluation system using PEPCK promoter-luciferase").

The concentration of administration of adiponectin when the adiponectin-containing appetite control agent for oral administration of the present invention is to be administered in a liquid form can be appropriately determined; for example, it can be determined with reference to its content in mother milk, i.e., 10 ng/ml-20 ng/ml (L. J. Martin et al., Am J Clin Nutr 2006, Vol. 83, p 1106-1011), from the viewpoint that no detrimental effect in oral administration is observed.

When the adiponectin-containing appetite control agent for oral administration of the present invention is to be administered in a solid or liquid form, the amount of administration and the content of adiponectin can be appropriately adjusted. In particular, when a transgenic strawberry fruit is used as a source of adiponectin, they can be adjusted as follows. Namely, fruits harvested are collected as one group (=one batch; here, one batch can be arbitrary defined with consideration given to cultivation section, harvest period, line of recombinant, etc.), and all the fruits in each batch are processed by freeze grinding (or by extraction of juice), etc., then adiponectin concentration in the batch is measured. Then non-recombinant strawberry fruits are appropriately mixed in the batch, to adjust the amount of administration and the content of adiponectin. Thus, the content of recombinant adiponectin can be controlled depending on the health conditions of users.

Below, the present invention is explained in further detail with reference to examples; however, the present invention is not limited to these embodiments.

EXAMPLES

1. Evaluation of Activity of Adiponectin by its Oral Administration

A purified adiponectin preparation (recombinant human adiponectin, R&D Systems) was dissolved in phosphate buffer saline (PBS) (composition: 137 mM sodium chloride, 2.7 mM potassium chloride, 10 mM disodium hydrogen phosphate, 1.8 mM monobasic potassium phosphate, pH 7.4) at a concentration of 10 µg/20 µl, and the obtained adiponectin solution was orally administered to a mouse (Balb/c, 8-week old female) having a standard body shape at an amount of 20 µl each time. As control, mice were orally administered with PBS alone at 20 µl each time. Administration was performed 5 consecutive days, and 6 hr after the final administration, the spinal cords of the mice were dislocated and internal organs (liver, spleen) were removed as samples. Each sample was immersed in RNALater (Ambion, Inc.), then frozen at −80° C. mRNA was extracted from the frozen samples, and subjected to DNA microarray analysis using Gene Chip from Affimetrix (Mouse Genome 430 2.0, 1-cycle target labeling protocol). Data of the administration group and control group were compared, and genes exhibiting enhanced expression or inhibited expression were identified.

Figure 1:
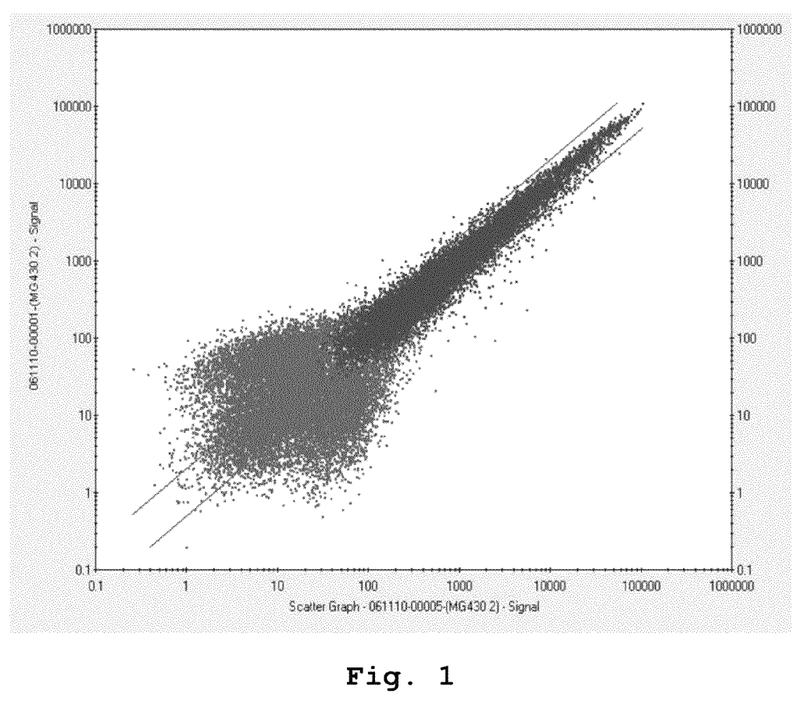
FIG. 1 shows comparison of gene-expression profile of the liver of mice orally administered with an adiponectin preparation (control: PBS administration).
Figure 2:
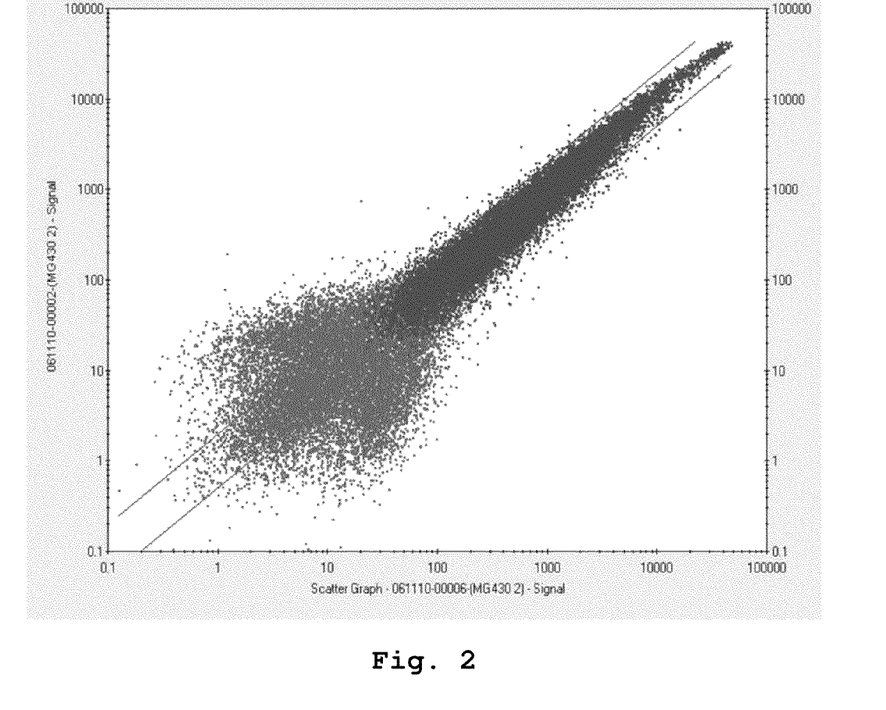
FIG. 2 shows comparison of gene-expression profile of the spleen of mice orally administered with an adiponectin preparation (control: PBS administration).

Comparison of gene-expression profile between the administration group and control group was represented by a scatter plot (FIGS. 1 and 2). In the liver in which an adiponectin receptor is present, there were 150 genes exhibiting enhanced expression (5 times or more), while there were 64 genes exhibiting inhibited expression (⅕ or less).

Genes exhibiting enhanced expression include the following: ELAV-like 2, defensin beta 8, DEAD box polypeptide 24, CKLF-like MARVEL transmembrane domain containing 2A, early B-cell factor 3, SH3-domain kinase binding protein 1, olfactomedin 3, Kinesin family member 16B, leucine rich repeat containing 52, Septin 11, tripartite motif-containing 36, catenin delta 1, opioid receptor mu 1, phosphatase and actin regulator 1, protein phosphatase 1 regulatory (inhibitor) subunit 9A, transient receptor potential cation channel, regulator of G-protein signaling 18, Spire homolog 1, zinc finger protein 423, chemokine ligand 15, junction adhesion molecule 2, ubiquitin-activating enzyme E1, Rho GTPase activating protein 23, Ssu72 RNA polymerase II CTD phosphatase homolog, Yipl domain family member 6, Cdc2-related kinase, arginine/serine-rich, DCP1 decapping enzyme homolog b, syndecan binding protein, F-box and WD-40 domain protein 19, nucleoporin 153, Thyroid hormone receptor beta, prolactin-like protein C 1, Shc SH2- domain binding protein 1, FAT tumor suppressor homolog 4, amiloride-sensitive cation channel 3, Eyes absent 3 homolog, testis expressed gene 13,
RGM domain family: member B, methyl-CpG binding domain protein 3-like 2, mesoderm posterior 2, prostaglandin F receptor, nucleolar complex associated 2 homolog, potassium voltage-gated channel (shaker-related subfamily member 4), ankyrin repeat domain 44, MYST histone acetyltransferase monocytic leukemia 4, fibronectin type III domain containing 1, pantothenatekinase (Hallervorden-Spatz syndrome), Lemur tyrosine kinase 2, cyclic nucleotide gated channel alpha 2, RAD54 like, carbonic anhydrase 3, PR domain containing 8, Chaperonin subunit 4 (delta), SAM domain and HD domain 1,
chromodomain helicase DNA binding protein 8, sperm associated antigen 1, Phosphofurin acidic cluster sorting protein 1, ribonucleotide reductase M2 B (TP53 inducible), six transmembrane epithelial antigen of prostate 2, Neural cell adhesion molecule 1, Ubiquitin-conjugating enzyme E2R 2, TAF11 RNA polymerase II, SMC6 structural maintenance of chromosomes 6-like 1, fibroblast growth factor 4, Rho guanine nucleotide exchange factor 15, SMC2 structural maintenance of chromosomes 2-like 1, heparin-binding EGF-like growth factor, Calcium channel, Serine/arginine repetitive matrix 1,
protocadherin beta 15, DEAD box polypeptide 25, seminal vesicle antigen-like 2, similar to late cornified envelope protein, protein kinase cAMP dependent regulatory: type II beta, coagulation factor II (thrombin) receptor-like 3, tetratricopeptide repeat domain 9, intraflagellar transport 57 homolog, IQ motif and Sec7 domain 1, diacylglycerol kinase iota, Protein kinase (cGMP-dependent type I), cofactor required for Sp1 transcriptional activation subunit 6, SWI/SNF related, vomeronasal 1 receptor D4, ATPase, Na+/K+ transporting (alpha 1 polypeptide), cholinergic receptor, ELAV-like 4, solute carrier family 25 member 31.

Genes exhibiting inhibited expression include the following: histocompatibility 2K region, growth arrest and DNA-damage-inducible 45 gamma, sema domain (semaphorin) 4D, transformation related protein 53, matrix metallopeptidase 14 (membrane-inserted), regulator of G-protein signaling 16, phosphatidylinositol-4-phosphate 5-kinase, type 1 beta, ATP-binding cassette sub-family F (GCN20) member 1, HCF-binding transcription factor Zhangfei, methionine aminopeptidase 2, ring finger protein 2, ubiquitin-conjugating enzyme E2C, prosaposin, arylacetamide deacetylase-like 1, nuclear factor I/X, glucose-6-phosphate dehydrogenase X-linked, vesicle-associated membrane protein, ADP-ribosylation factor 4-like, CCAAT/enhancer binding protein beta, nuclear receptor subfamily 0 group B member 2, spastic paraplegia 20, DNA-damage-inducible transcript 4, cyclin-dependent kinase 5: regulatory subunit (p35) 1, methyltransferase like 7A, sialic acid binding Ig-like lectin 1, insulin-like growth factor binding protein 1, solute carrier organic anion transporter family: member 1a1, PRP40 pre-mRNA processing factor 40 homolog A, GNAS complex locus, amyloid beta (A4) precursor-like protein 2, phosphoenolpyruvate carboxykinase 1, interleukin 2 receptor gamma chain, TSC22 domain family 3, solute carrier family 45 member 3, macrophage receptor with collagenous structure, ectonucleoside triphosphate diphosphohydrolase 1.

In the spleen, 52 genes exhibited enhanced expression, and 109 genes exhibited inhibited expression.

These results clearly showed that when an adiponectin-containing composition is orally administered, gene expression is altered. That is, the following general speculation has been denied: when adiponectin is ingested, it is digested and decomposed through the food digestive process, and therefore no effect of adiponectin should be exhibited; thus, usefulness of the ingestion of adiponectin has been clearly demonstrated. This is particularly useful in that adiponectin is ingested in a normal manner, different from pharmaceutical agents for oral administration such as enteric coated pharmaceutical agents used for drug delivery; thus suggesting that effects of adiponectin can be obtained through ingestion of an adiponectin-containing food composition.

2. Production of Strawberry that Expresses Human Adiponectin (1) Making Artificial Synthetic Gene of Human Adiponectin A long primer encoding the translated region (position 85-816) of human adiponectin gene (NCBI Accession No. NM_004797) (hereinafter, also described as hAdi) was artificially synthesized and the translated region of this gene was produced by overlap method. This artificial synthetic gene was introduced in a pGEM-T vector (Promega) by TA cloning method, to produce pGEM-bαLA. The introduced plasmid pGEM-bαLA was collected through transformation of E. coli, and was subjected to sequence analysis to determine its gene sequence.

(2) Making Human Adiponectin Gene for Expression in Plant

Next, using the clone pGEM-hAdi as a template after its sequence confirmation, PCR with adapter-primer was performed to add restriction enzyme recognition sequence and tag sequence. Namely, a gene having Bam HI, Xba I recognition sequence on the side of 5' terminal, and His-Tag (6×His), KDEL sequence, stop codon and Sac I recognition sequence on the side of 3' terminal was produced. This gene was cloned into pGEM-T Vector (Promega) to obtain pGEM-hAdi/His+KDEL.

(3) Integration of Human Adiponectin Gene into Plant Expression Vector pBE2113

A plant expression vector pBE2113-GUS (Mitsuhara et al. (1996) Plant and Cell Physiology Vol. 37, No. 1, p 49-59) was simultaneously digested with restriction enzymes Xba I/Sac I, then subjected to CLAP processing. Meanwhile, with respect to cDNA fragments of the human adiponectin gene, pGEM-hAdi/His+KDEL was simultaneously digested with restriction enzymes Xba I/Sac I to cut out and collect the gene region of interest. The vector side and cDNA fragments were mixed and processed with ligase to produce pBE-hAdi (FIG. 3).

Figure 3:
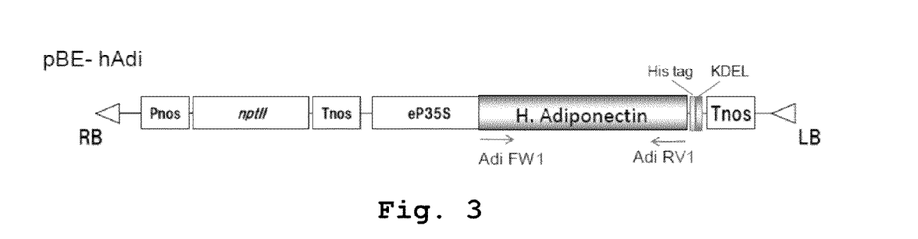
FIG. 3 shows pBE-hAdi produced using a plant expression vector pBE2113 modified with a human adiponectin gene.

Here, each abbreviation in FIG. 3 represents the following: Pnos: nopaline synthase promoter, nptII: neomycin phosphotransferase II, Tnos: nopaline synthase terminator, eP35S: cauliflower mosaic virus 35S promoter, H. Adiponectin: human adiponectin gene (SEQ ID NO 1), AdiFW1: AdiFW1 primer (SEQ ID NO 3) recognition region, AdiRV1: AdiRV1 primer (SEQ ID NO 4) recognition region, His tag: histidine tag, KDEL: endoplasmic reticulum retention signal.

(4) Transformation of Strawberry (Production of Km-Resistant Stain)

The human-adiponectin-gene plant expression vector pBE-hAdi was introduced in an agrobacterium (Agrobacterium tumefaciens strain LBA4404) by direct introduction method. The obtained kanamycin (Km)-resistant strain (introduced plasmid confirmed) was used for strawberry transformation test. Km-added medium was used for callus induction and re-differentiation, to select a Km-resistant individual.

(5) Confirmation of Introduction of Human Adiponectin Gene in Transgenic Strawberry Strain (Km-Resistant Strain)

Figure 4:
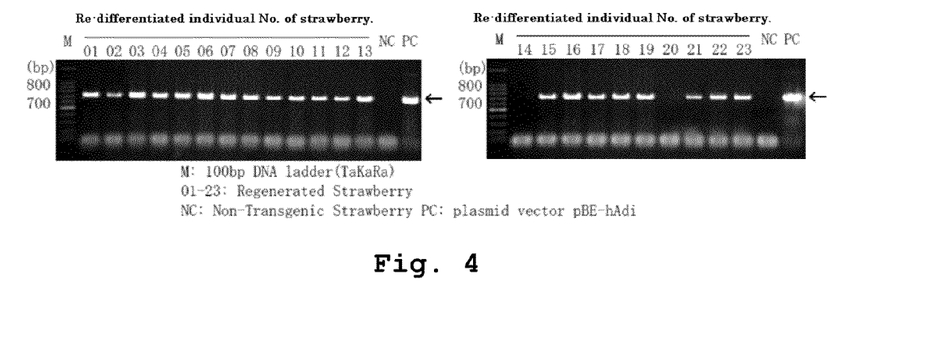
FIG. 4 shows an electrophoretogram to confirm introduction of human adiponectin gene into transgenic strain of strawberry (Km-resistant strain) by genomic PCR.

Specific primer AdiFW1 (forward primer) and AdiRV1 (reverse primer) set at the both ends of a human adiponectin gene were used to carry out genomic PCR. For the extraction of genomic DNA, a nucleic acid extraction kit MagExtractor-Plant Genome-(TOYOBO) was used in accordance with the protocol for using a nucleic acid purification system MagExtractor MFX-6100 (TOYOBO). PCR products were detected by electrophoresis using 1.5% TBE agarose gel. As a result, of the 23 samples tested, the objective amplified fragments (732 bp) were detected in 21 samples and gene introduction was confirmed (FIG. 4).

```
AdiFW1 primer sequence:
                                    (SEQ ID NO 3)
5'-ATGCTGTTGCTGGGAGCTGTTCTA-3'

AdiRV1 primer sequence:
                                    (SEQ ID NO 4)
5'-GGTGTCATGGTAGAGAAGAAAGCC-3'
```

(6) Selection of Human Adiponectin High-Expression Line

Using Human Adiponectin/Acrp30 immunoassay (Quantikine) (R&D systems), and in accordance with the attached protocol, ELISA was performed. Leaf tissues were collected from 100 lines of cultured strains (each referred to as line No. 1 to line No. 100), triturated under the presence of liquid nitrogen, and added with a grinding buffer (potassium phosphate buffer, pH 7.0, 1% Triton X-100, protease inhibitor (Roche Diagnostics GmbH; concentration: 1 tablet/25 ml)) in an amount 5 times the weight of the raw tissue; then the centrifuged supernatant of the grinding solution obtained was used as an assay sample.

Figure 5:
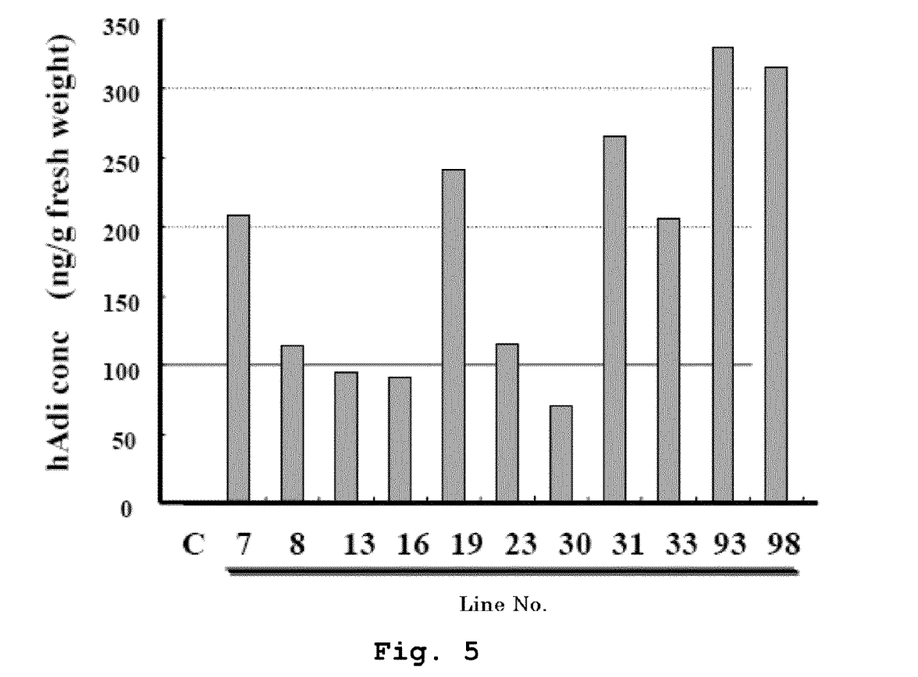
FIG. 5 is a graph showing adiponectin concentrations in human adiponectin high-expression lines.

As a result, a strain which exhibits 200 ng/gFW or more of expression was confirmed (FIG. 5). Here, when the amount of expression is 200 ng/gFW or more, one strawberry fruit of a standard size (approximately 10 g) can provide the amount of adiponectin contained in 100 ml of mother milk.

(7) Confirmation of Expression by Western Blotting

In order to carry out protein analysis of human adiponectin expressed by strawberry, Western blotting was performed. Strawberry samples were prepared similar to those for ELISA (described above in (6)). SDS-PAGE was performed in Laemmli buffer system into which a reducing agent (2-Me) was added, using precast gel SDS-PAGE Mini 10% (TEFCO), then the separated protein was transferred to Hybond-P (GE Healthcare, Inc.). The obtained blot was blocked by an ECL blocking agent (GE Healthcare Inc.), and reacted with a primary antibody: Mouse anti-adiponectin, human monoclonal antibody (CHEMICON) in a 5,000-times diluting solution, and with a secondary antibody: Anti-Mouse IgG-Peroxidase, Goat (SIGMA) in a 10,000-times diluting solution, and detected by ECL plus Western Blotting Detection Reagents (GE Healthcare, Inc.).

Figure 6:
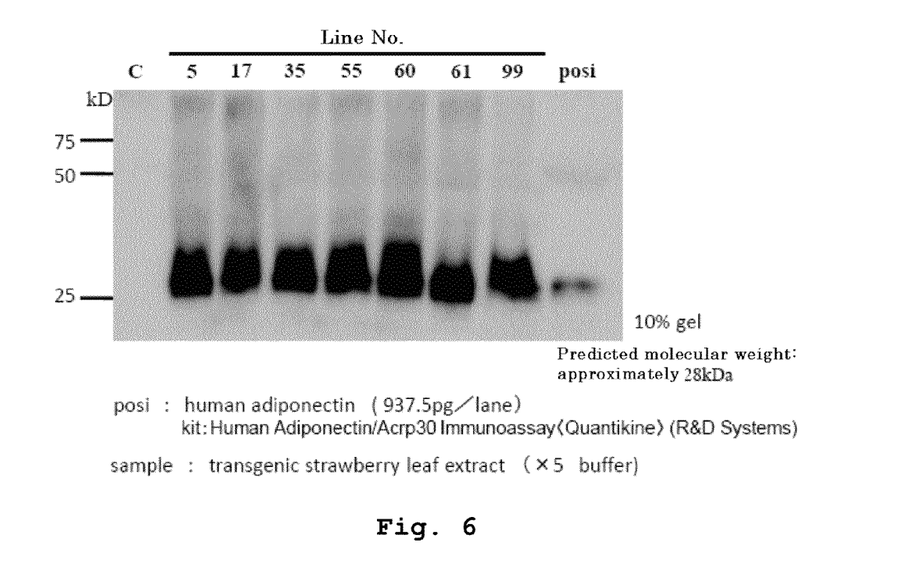
FIG. 6 shows Western blotting of human adiponectin high-expression lines.

Analytical result showed a band at the position of expected molecular weight (28 kDa), confirming the expression of human adiponectin in the leaf tissue (FIG. 6).

Figure 7:
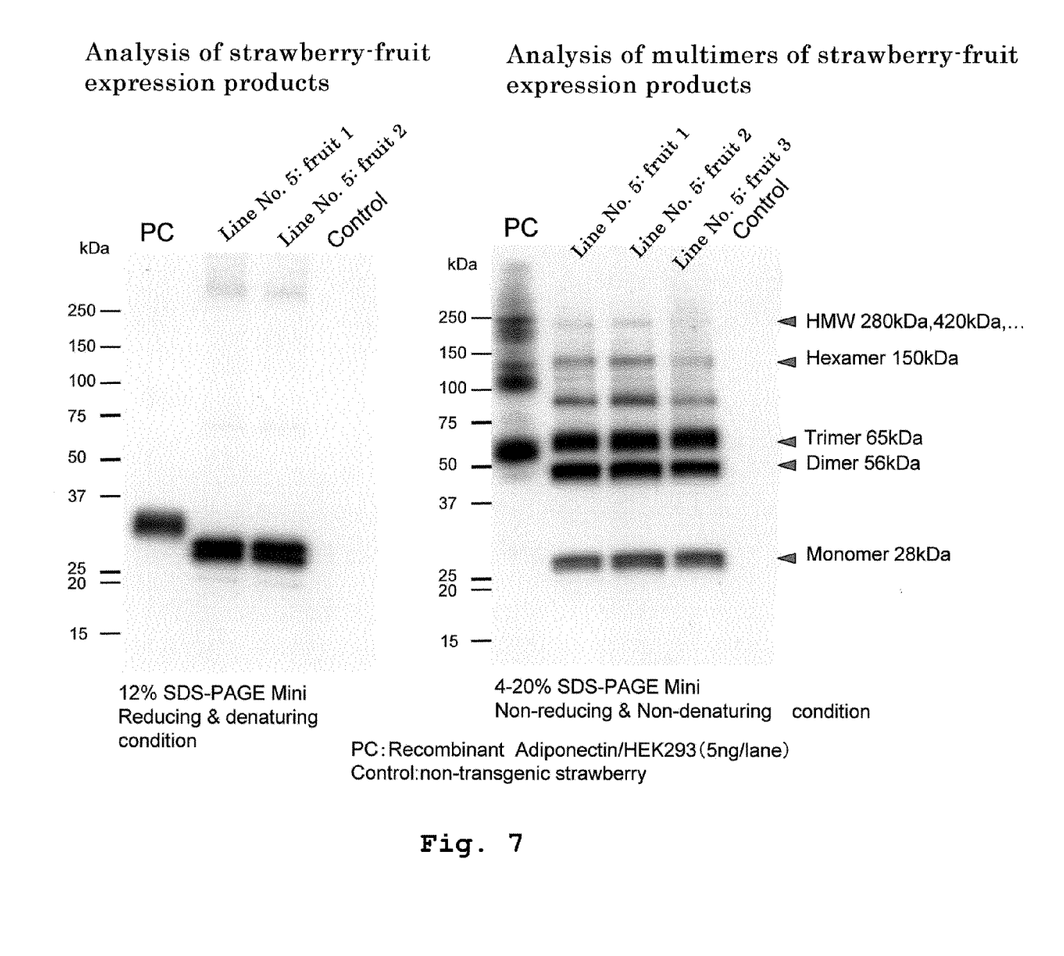
FIG. 7 shows Western blotting of human adiponectin expressed by strawberry fruits.

(8) Expression Analysis in the Fruits of Human Adiponectin High-Expression Strawberry Line We attempted to confirm expression of human adiponectin and occurrence/non-occurrence of multimer formation in strawberry fruits. Human adiponectin high-expression line No. 5 (hereafter, also simply referred to as line No. 5) was cultivated and its fruits were harvested. Strawberry fruit samples were triturated under the presence of liquid nitrogen, and added with a grinding buffer (potassium phosphate buffer, pH 7.0, 1% Triton X-100, protease inhibitor (Roche Diagnostics GmbH; concentration: 1 tablet/25 ml)) in an amount 3 times the weight of the raw sample; then the centrifuged supernatant of the grinding solution obtained was used as a protein extract. In this sample, a Laemmli sample buffer (BIO-RAD) was added to adjust the amount of protein at 16.5 µg/lane, and the sample was subjected to SDS-PAGE using precast gel SDS-PAGE Mini 12% (TEFCO), then Western blotting was performed in accordance with the protocol (reduction processing) similar to those described in (7). As a result, similar to the case of leaf sample, 2 bands were confirmed at the position of approximately 28-kDa, which is the expected molecular weight of monomers (FIG. 7).

Next, for the purpose of multimer analysis, a sample buffer without a reducing agent (2% SDS, 20M Tris-HCl pH 6.8, 10% Glycerol, 0.05% BPB, 0.05% XC) was added to the protein extract. The amount of protein was adjusted to be 16.5 µg/lane, and the sample was incubated for 30 min, and without heat treatment, it was subjected to SDS-PAGE using 4-20% gradient SDS gel (TEFCO), then Western blotting was performed similar to the above (7). As a result, multiple bands were confirmed in a region of molecular weight larger than that of the monomers, suggesting the formation of multimers in the transgenic strawberry fruits (FIG. 7).

From the above results, human adiponectin expressed by strawberry was confirmed to form a multimer. Adiponectin molecules do not form a monomer in the body, but form a trimer, hexamer, dodecamer and larger multimers, and these multimers are presumed to be in activated forms. Accordingly, the above results suggest that the human adiponectin expressed in the transgenic strawberry leaf tissue is also in an activated form.

3. Evaluation System of Adiponectin Using PEPCK Promoter-Luciferase

We constructed an activity measurement system by fluorescence using a promoter of phosphoenolpyruvate carboxykinase (PEPCK), the expression of which is inhibited by adiponectin, and using luciferase as a reporter gene. A lentivirus vector system was employed in the activity measurement system. As a plasmid construct constituting the vector, existing ones (packaging plasmid, envelope & Rev plasmid and self-inactivating (SIN) vector plasmid) were used, to which the following modifications were added to construct the adiponectin activity measurement system. Namely, the envelope was converted to the G-glycoprotein of vesicular stomatitis virus (VSV) to widen its host range. In the SIN vector plasmid, mouse and human PEPCK promoters (each obtained from genomic DNA) were introduced in the promoter region, and luciferase gene (Gaussia Luciferase modified to human codon: GLuc) was integrated in their downstream. Furthermore, in the downstream of GLuc, a SV40 promoter and hygromycin-resistant gene were integrated in order to provide drug selectivity. The above retrovirus vector was thus constructed, which was transfected in packaging cells to obtain infected viral particles.

Figure 8:
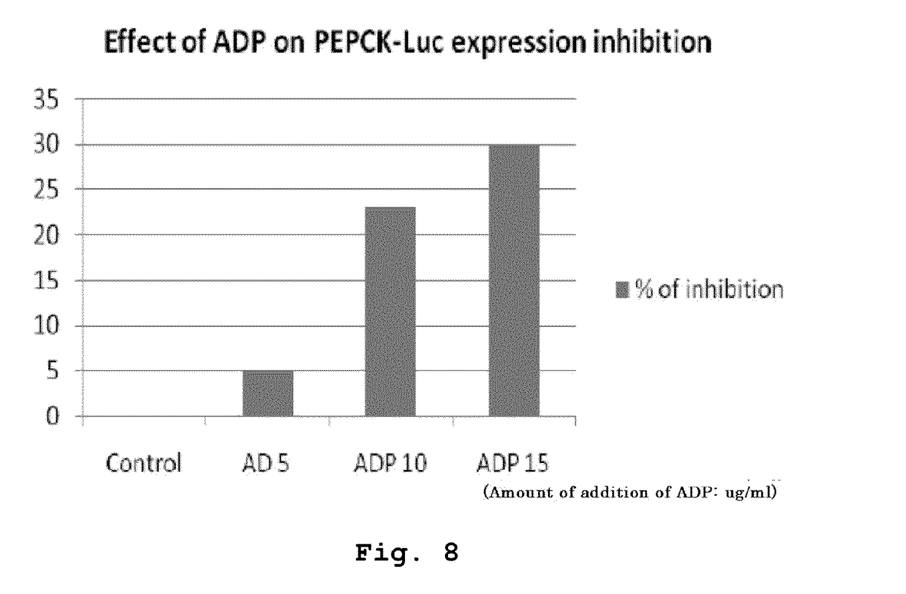
FIG. 8 shows luciferase activity when assay cell line (Huh7) is infected with constructed retrovirus and added with adiponectin.

This virus was infected to the assay cells (Huh7), and the luciferase activity upon addition of adiponectin was measured. FIG. 8 shows the result.

The inhibition of expression depending on the concentration was confirmed, demonstrating that this system can to be sufficiently used as an adiponectin measurement system.

4. DNA Microarray Test in Mice Orally Administered (Ingested) with Adiponectin

Mice with a standard body shape were prepared as the following control group and administration group, to perform experiments.

Control group: strawberry fruit (non-recombinant)
Administration group: adiponectin-expressing strawberry fruit (freeze-dried fruit, adiponectin content: 42 µg/g of dry weight)

In the control group and administration group, 5 mice (Balb/c, 7-week-old male) were placed in a same gage, and they were subjected to free feeding (0.2 g of dry weight) for 6 hr a day for 5 consecutive days of administration. The adiponectin content contained in the transgenic strawberry fruits taken by one mouse in the administration group was estimated to be approximately 8.4 µg/day.

After consecutive 5-day administration, the spinal cords of the mice in each group were dislocated at 6 hr after the final administration, then internal organs (liver, spleen, small intestine) were removed as samples. Each sample was immersed in RNALater (Ambion, Inc.), then frozen at −80° C. mRNA was extracted from the frozen samples, and subjected to DNA microarray analysis using Gene Chip from Affimetrix (Mouse Genome 430 2.0, 1-cycle target labeling protocol). Data of the administration group and control group were compared, and genes exhibiting enhanced expression or inhibited expression were identified.

Figure 9:
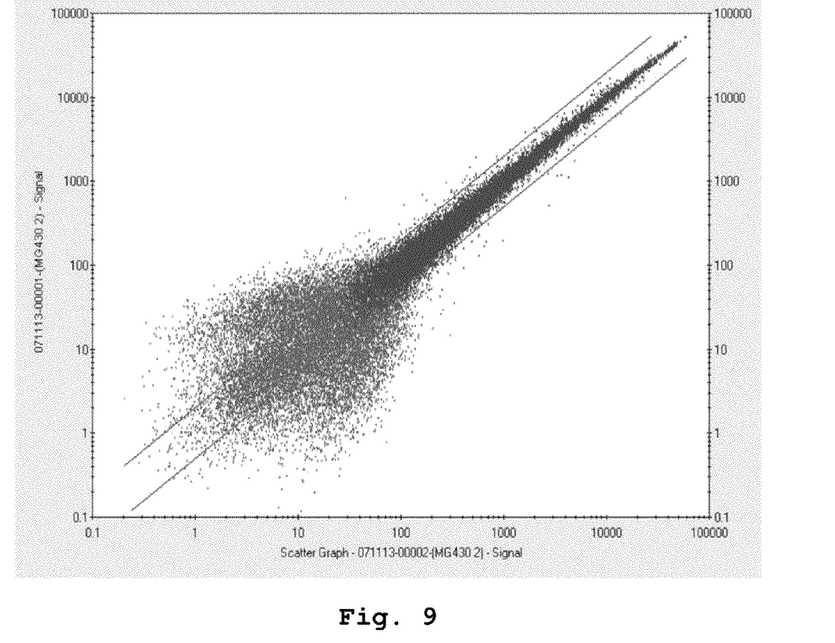
FIG. 9 shows comparison of gene-expression profile of the liver of mice orally administered with (ingesting) adiponectin-expressing strawberry (control: administration of non-transgenic strawberry).
Figure 10:
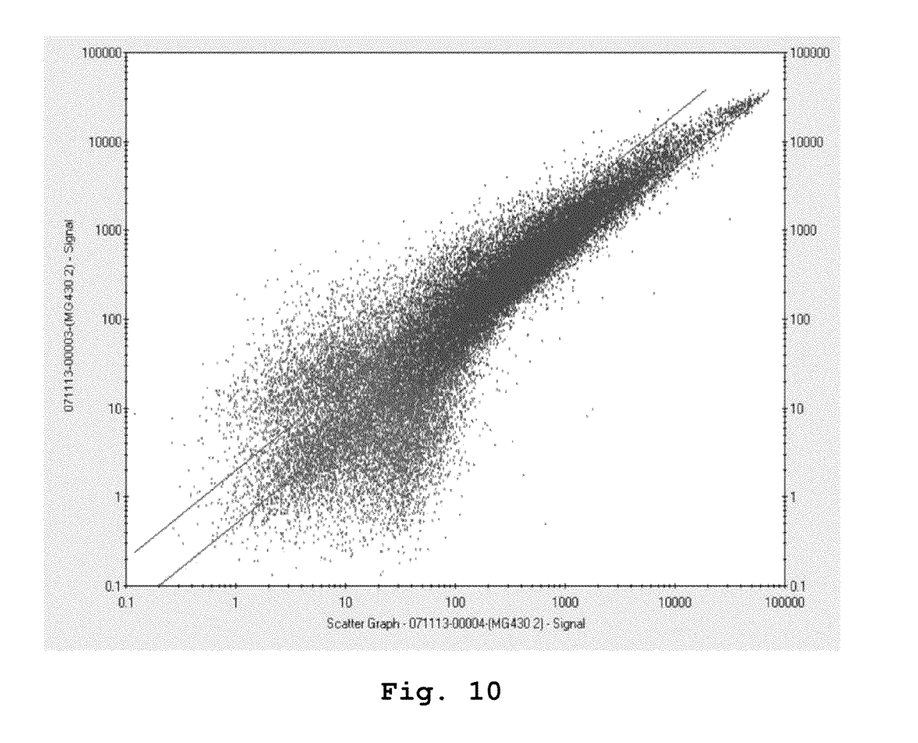
FIG. 10 shows comparison of gene-expression profile of the spleen of mice orally administered with (ingesting) adiponectin-expressing strawberry (control: administration of non-transgenic strawberry).
Figure 11:
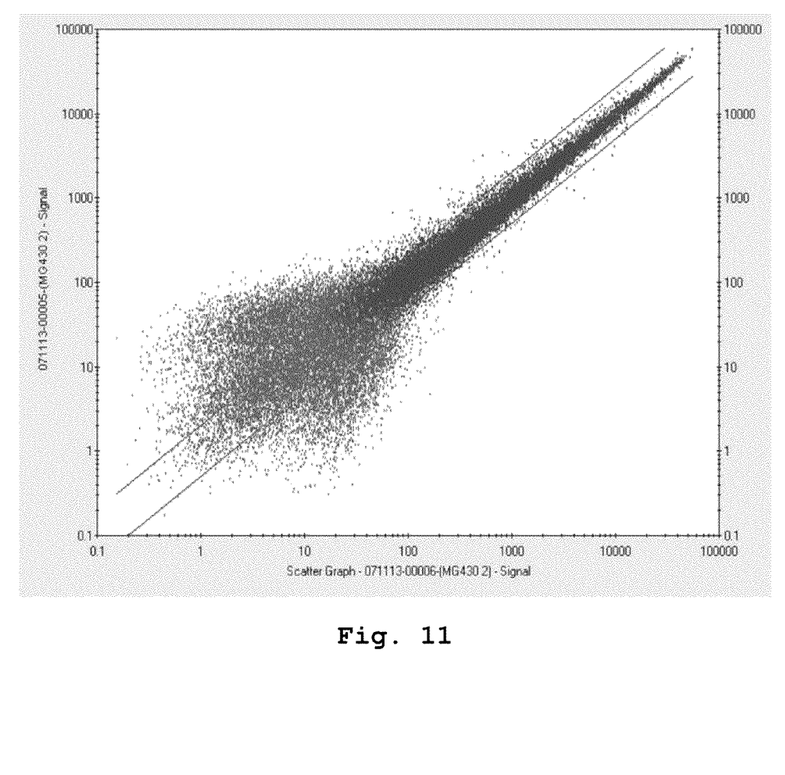
FIG. 11 shows comparison of gene-expression profile of the small intestine of mice orally administered with (ingesting) adiponectin-expressing strawberry (control: administration of non-transgenic strawberry).

Comparison of gene-expression profile between the administration group and control group was represented by a scatter plot (FIGS. 9 to 11). In the liver in which an adiponectin receptor is present, there were 10 genes exhibiting enhanced expression (5 times or more), while there were 58 genes exhibiting inhibited expression (⅕ or less).

Genes exhibiting enhanced expression include the following: parathyroid hormone receptor 2, sodium channel (voltage-gated) type II alpha 1, Chemokine (C—C motif) receptor 9, potassium voltage gated channel Shaw-related subfamily member 3, tankyrase TRF1-interacting ankyrin-related ADP-ribose polymerase, thioredoxin-like 1, tumor necrosis factor receptor superfamily member 12a.

Genes exhibiting inhibited expression include the following: RAD51 associated protein 1, pleckstrin homology domain interacting protein, FAST kinase domains 3, tryptase beta 2, solute carrier family 35 member F2, hemoglobin Z beta-like embryonic chain, scrapie responsive gene 1, leucine rich repeat containing 34, coiled-coil domain containing 38, Nephronectin, calcium channel voltage-dependent N type alpha 1B subunit, interleukin 7 receptor, ST6-N-acetylgalactosaminide alpha-2,6-sialyltransferase 1, neurexophilin 1, cellular retinoic acid binding protein I, adult male hippocampus cDNA, layilin, Eph receptor A7, secretory blood group 1, lysyloxidase, serine peptidase inhibitor Glade A member 1f, trophoblast glycoprotein, anaplastic lymphoma kinase, cytochrome P450 family 26 subfamily a polypeptide 1, zinc finger protein 352, synapsin II, Catenin alpha 1, RUN and TBC1 domain containing 2, kinesin family member 2C.

In other organs, there were 503 genes in the spleen and 238 genes in the small intestine exhibiting enhanced expression, and 417 genes in the spleen and 4 genes in the small intestine exhibiting inhibited expression.

The above results showed that ingestion of adiponectin induces changes in the expression states of extremely large number of genes; changes are particularly induced in the expression of genes relating to glucose metabolism and appetite control.

5. Peptide Marker Array (Obesity-Related) Test in Mice Orally Administered with (Ingesting) Adiponectin Serum was collected from the control group and the administration group in the above experiment (4), and used in the peptide marker array (obesity-related) test. As the peptide marker array, Obesity Peptide Biomarker Array from PHOENIX Pharmaceuticals and Obesity Biomarker Chip (Rat, Mouse) were used, and the analysis was performed in accordance with the manufacturer's protocol.

From the result of the peptide marker array (obesity-related) analysis, as an overall tendency, behaviors of peptides relating to glucose metabolism and peptides relating to appetite control were confirmed in the administration group. Representative results were shown in Table 1 (increases by ingestion of transgenic strawberry) and Table 2 (decreases by ingestion of transgenic strawberry). Here, regarding all the peptides in the tables, information such as their peptide sequence and roles in the live body is provided from international databases, for example, National Center for Biotechnology Information (NCBI): URL:http://www.ncbi.nlm.nih.gov/.

TABLE 1

| Peptide name | Administration group/control group |
|---|---|
| Ghrelin | 1.370298772 |
| NPY | 1.238886596 |
| Bombesin | 1.198294051 |

TABLE 2

| Peptide name | Administration group/control group |
|---|---|
| ACTH | 0.738482065 |
| MCH | 0.760748062 |
| Autotaxin | 0.80963451 |

In particular, Ghrelin and neuropeptide Y (NPY) which exhibit significant improvement are peptides involved in the enhancement of food intake. ACTH exhibiting a significant decrease is a peptide involved in the inhibition of food intake.

From the above results, we consider that by means of ingestion of adiponectin, behaviors of peptides relating to glucose metabolism and appetite control are changed, thus producing an action of appetite control in individuals taking adiponectin.

6. Biochemical Analysis in the Blood of Mice Orally Administered with (Ingesting) Adiponectin Using mice with a standard body shape, the following groups A-C were prepared to perform the experiment.
A: General feed+human adiponectin-expressing strawberry fruit
B: General feed+non-recombinant strawberry fruit
C: General feed (control)

In each group, 14 mice (Balb/c, 7-week-old male) were placed in a same gage, and they were subjected to free feeding for 6 hr a day for 10 or 20 consecutive days of administration. Here in groups A and B, strawberry homogenate was added to the general feed (equivalent amount of 2 ml/mouse). The homogenate of human adiponectin-expressing strawberry fruit of the group A contains 1.2 µg/2 ml of recombinant adiponectin. Serum were collected from 5 mice at 10 days after administration, and from the remaining 9 mice at 20 days after administration, both at 6 hr after the final administration, and the glucose content of the serum was measured.

Figure 12:
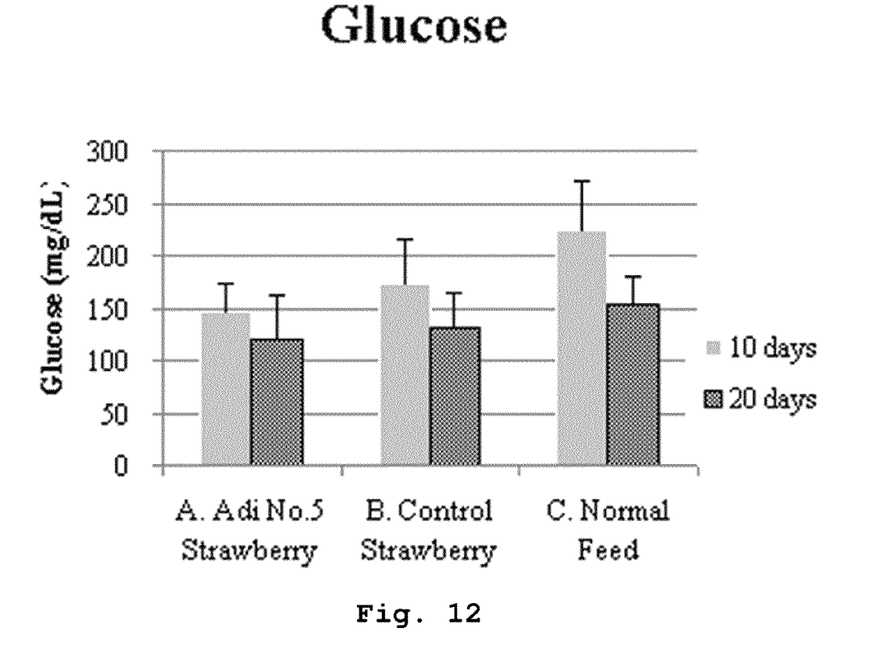
FIG. 12 shows biochemical analysis (glucose content) of the serum of mice orally administered with (ingesting) adiponectin-expressing strawberry.

FIG. 12 shows the serum glucose content. The glucose content of group A in which general feed+adiponectin-expressing strawberry were administered showed the lowest value at both 10 days and 20 days after administration, compared to other groups. This result suggested that oral administration of recombinant human adiponectin expressed in strawberry can promote decreases of blood glucose levels.

INDUSTRIAL APPLICABILITY

With the present invention, when a food composition containing adiponectin is ingested, control of appetite such as enhanced food intake is possible. In particular, the enhancement effect of food intake by the promotion of ghrelin secretion due to ingestion of adiponectin is a new finding achieved during the research of the present invention.

The invention claimed is:

1. A method for preparation of an appetite enhancer for oral administration, comprising
using a strawberry fruit of a transformed strawberry that expresses a gene encoding human adiponectin to prepare the appetite enhancer for oral administration.

2. The method according to claim 1, wherein the transformed strawberry that expresses adiponectin is a transformed strawberry in which a gene consisting of
(a) a DNA consisting of the base sequence set forth in SEQ ID NO: 1, or
(b) a DNA that has a homology of 99.5% to the DNA consisting of the base sequence set forth in SEQ ID NO: 1, and that encodes a polypeptide having an adiponectin activity,
is introduced.

3. The method according to claim 1, wherein the transformed strawberry that expresses adiponectin is a transformed strawberry in which a gene encoding
(a) a polypeptide consisting of the amino acid sequence set forth in SEQ ID NO: 2, or
(b) a polypeptide that consists of an amino acid sequence in which one to ten amino acids are replaced in the amino acid sequence set forth in SEQ ID NO: 2, and that has an adiponectin activity,
is introduced.

4. A method for enhancing appetite in a subject, comprising orally administering to a subject in need of such appetite enhancement an effective amount of the appetite enhancer for oral administration prepared by the method according to claim 1.

* * * * *

SEQUENCE LISTING

<160> NUMBER OF SEQ ID NOS: 4

<210> SEQ ID NO 1
<211> LENGTH: 735
<212> TYPE: DNA
<213> ORGANISM: Homo sapiens

<400> SEQUENCE: 1

```
atgctgttgc tgggagctgt tctactgcta ttagctctgc ccggtcatga ccaggaaacc      60
acgactcaag gcccggagt cctgcttccc ctgcccaagg gggcctgcac aggttggatg     120
gcgggcatcc cagggcatcc gggccataat ggggccccag gccgtgatgg cagagatggc     180
accctggtg agaagggtga gaaggagat ccaggtctta ttggtcctaa gggagacatc     240
ggtgaaaccg gagtacccgg ggctgaaggt ccccgaggct ttccgggaat ccaaggcagg     300
aaaggagaac ctggagaagg tgcctatgta taccgctcag cattcagtgt gggattggag     360
acttacgtta ctatccccaa catgcccatt cgctttacca agatcttcta caatcagcaa     420
aaccactatg atggctccac tggtaaattc cactgcaaca ttcctgggct gtactacttt     480
gcctaccaca tcacagtcta tatgaaggat gtgaaggtca gcctcttcaa gaaggacaag     540
gctatgctct tcacctatga tcagtaccag gaaaataatg tggaccaggc ctccggctct     600
gtgctcctgc atctggaggt gggcgaccaa gtctggctcc aggtgtatgg ggaaggagag     660
cgtaatggac tctatgctga taatgacaat gactccacct tcacaggctt tcttctctac     720
catgacacca actga                                                     735
```

<210> SEQ ID NO 2
<211> LENGTH: 244
<212> TYPE: PRT
<213> ORGANISM: Homo sapiens

<400> SEQUENCE: 2

```
Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
        35                  40                  45

His Asn Gly Ala Pro Gly Arg Asp Gly Arg Asp Gly Thr Pro Gly Glu
    50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160
```

```
Ala Tyr His Ile Thr Val Tyr Met Lys Asp Val Lys Val Ser Leu Phe
                165             170             175

Lys Lys Asp Lys Ala Met Leu Phe Thr Tyr Asp Tyr Gln Glu Asn
        180             185             190

Asn Val Asp Gln Ala Ser Gly Ser Val Leu Leu His Leu Glu Val Gly
        195             200             205

Asp Gln Val Trp Leu Gln Val Tyr Gly Glu Gly Glu Arg Asn Gly Leu
    210             215             220

Tyr Ala Asp Asn Asp Asn Asp Ser Thr Phe Thr Gly Phe Leu Leu Tyr
225             230             235             240

His Asp Thr Asn

<210> SEQ ID NO 3
<211> LENGTH: 24
<212> TYPE: DNA
<213> ORGANISM: Artificial
<220> FEATURE:
<223> OTHER INFORMATION: A forward primer for human Adiponectin gene

<400> SEQUENCE: 3
atgctgttgc tgggagctgt tcta                                          24

<210> SEQ ID NO 4
<211> LENGTH: 24
<212> TYPE: DNA
<213> ORGANISM: Artificial
<220> FEATURE:
<223> OTHER INFORMATION: A reverse primer for human Adiponectin gene

<400> SEQUENCE: 4
ggtgtcatgg tagagaagaa agcc                                          24
```